United States Patent [19]

Goodwin et al.

[11] 4,110,543
[45] Aug. 29, 1978

[54] METHOD OF PREPARING HYDROCARBYL-SUBSTITUTED CRESOLS

[75] Inventors: Thomas E. Goodwin, College Station, Tex.; Charles M. Starks, Ponca City, Okla.

[73] Assignee: Continental Oil Company, Ponca City, Okla.

[21] Appl. No.: 771,508

[22] Filed: Feb. 24, 1977

[51] Int. Cl.$^2$ .............................................. C07C 39/06
[52] U.S. Cl. ....................................... 568/781; 568/805
[58] Field of Search ........... 260/621 R, 621 D, 624 E, 260/624 C, 624 R, 666 A, 624, 626 T

[56] References Cited

U.S. PATENT DOCUMENTS

| | | | |
|---|---|---|---|
| 3,296,316 | 1/1967 | Neuworth | 260/621 D |
| 3,346,649 | 10/1967 | Leston | 260/624 C |
| 3,417,149 | 12/1968 | Neuworth | 260/621 D |
| 3,426,358 | 2/1969 | Schlichting | 260/621 R |
| 3,470,259 | 9/1969 | Leston | 260/621 D |
| 3,737,466 | 6/1973 | Sharp | 260/621 R |
| 3,933,927 | 1/1976 | Goddard | 260/624 E |

*Primary Examiner*—James O. Thomas, Jr.
*Assistant Examiner*—Werren B. Lone
*Attorney, Agent, or Firm*—Bayless E. Rutherford, Jr.

[57] ABSTRACT

A method of preparing hydrocarbyl-substituted cresols is disclosed. The method comprises heating a mixture of mono- or di-hydrocarbyl-substituted cresols and an alcohol, which is benzyl alcohol or a $C_1$–$C_{10}$ aliphatic alcohol, at an elevated temperature in the presence of a catalytic amount of alumina. The product contains at least one hydrocarbyl substituent corresponding to the hydrocarbon moiety of the alcohol used in the process. A typical process employs 4,6-di-t-butyl-m-cresol and isopropanol to prepare a product mixture containing a substantial amount of thymol.

3 Claims, No Drawings

METHOD OF PREPARING HYDROCARBYL-SUBSTITUTED CRESOLS

GENERAL BACKGROUND

It is well-known that cresols and methylated phenols are very useful materials. They may be used as resin intermediates, and as solvents for wire enamel. Also, they may be used as intermediates in the preparation of a variety of products such as pesticides, vitamins and nonflammable functional fluids.

It is known that alkylated cresols can be prepared from t-butyl-substituted cresols by two separate and distinct operations, namely debutylation and alkylation. It would be desirable, however, to accomplish this transformation in a single, continuous process. Our invention is directed to such a process (or method).

PRIOR ART

A search of the prior art produced only three references having any possible pertinency to the subject matter of the present invention. These references are U.S. Pat. Nos. 3,296,316; 3,346,649; and 3,470,259. The teachings of these patents are summarized below.

U.S. Pat. No. 3,296,316 teaches dealkylation of a mixture of 4-t-butyl-o-cresol and 4-6-di-t-butyl-o-cresol using aluminum phenoxide as the catalyst to produce o-cresol. It also teaches that aluminum phenoxide must be present in the system.

U.S. Pat. No. 3,346,649 teaches a method wherein 4,6-di-t-alkyl-3-lower alkylphenols are dealkylated by heating a 4,6-di-t-alkyl-3-lower alkylphenol in the presence of a catalytic amount of aryloxide of a metal which is zirconium, hafnium, niobium and tantalium. The product is 4-t-alkyl-3-lower phenol.

U.S. Pat. No. 3,470,259 teaches dealkylation of ortho-,para-ditertiary-alkyl-meta-cresols to give meta-cresol by heating the ortho-,para-ditertiary-alkyl-meta-cresols in the presence of a catalytic amount an aryloxide of a metal which is zirconium, niobium, hafnium or tantalium.

Applicants submit that a brief study of the teachings of these references show that they do not suggest the present invention.

BRIEF SUMMARY OF THE INVENTION

Briefly stated, the present invention is directed to a method of preparing hydrocarbyl-substituted cresols wherein the method comprises heating a mixture of (a) mono- or di-hydrocarbyl-substituted cresols and (b) an alcohol, which is benzyl alcohol or a $C_1$–$C_{10}$ aliphatic alcohol, at an elevated temperature in the presence of a catalytic amount of activated alumina.

In a preferred aspect, the present invention is directed to the preparation of cresols, polyalkylated phenols and alkylated cresols wherein the method comprises heating a mixture of (a) mono- or di-alkyl-substituted cresols and (b) a $C_1$–$C_{10}$ aliphatic alcohol at an elevated temperature in the presence of a catalytic amount of alumina.

In our process the hydrocarbyl substituent of the cresol feedstock is removed. The product contains at least one hydrocarbyl substituent corresponding to the hydrocarbon moiety of the alcohol used in the process.

Stated more briefly, our process is one wherein dealkylation and alkylation occur in the same step.

DETAILED DESCRIPTION

Materials Used

Suitable hydrocarbyl-substituted cresols for use in our process are represented by the formula

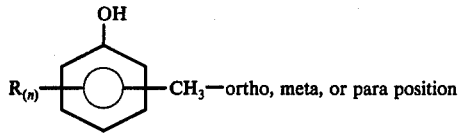

wherein R is a hydrocarbyl group substituted on any carbon atom other than that attached to the cresylic methyl group. R can be a cyclohexyl, 1-methylcyclohexyl, or a $C_4$–$C_6$ tertiary alkyl group, but preferably is a $C_4$–$C_6$ tertiary alkyl group, and $n$ is an integer of 1 or 2. Examples of suitable cresols include the following: 4,6-di-t-butyl-m-cresol, 2,6-di-t-amyl-p-cresol, 4,6-di-t-hexyl-o-cresol, 4-t-butyl-m-cresol, 2-t-amyl-p-cresol, 4,6-di-cyclohexyl-m-cresol, and 2-cyclohexyl-p-cresol.

Suitable alcohols include benzyl alcohol, isopropanol, and $C_1$–$C_{10}$ primary alkanols.

Suitable amounts of alcohol and cresol, expressed as moles alcohol to moles cresol, are in the range of about 0.2:1 to about 15:1. On the same basis, the preferred amounts of alcohol and cresols are in the range of about 0.5:1 to 5:1.

Any activated alumina is suitable for use in our process.

A preferred activated alumina for use in our process is one prepared by the hydrolysis of aluminum alkoxides. The preferred activated alumina has the following properties:

| | |
|---|---|
| Crystal Structure | α-alumina monohydrate |
| Surface Area, meters/gram | 230 – 300 |
| $Al_2O_3$, weight percent* | 70 – 75 |
| Loose bulk density, grams/liter | 650 –720 |

*substantially all of the remainder is water.

A particularly suitable activated alumina is available from Conoco Chemicals Division of Continental Oil Company under the trademark "CATAPAL" SB.

The amount of catalyst is related to the liquid hourly space velocity (LHSV)

$$LHSV = \frac{\text{volume of liquid* per hour}}{\text{volume of catalyst}}$$

*includes both cresol and alcohol

A suitable range of LHSV is about 0.1 to 35, with the preferred range being about 0.5 to 9.

PROCESS CONDITIONS

A suitable temperature range for conducting our process is in the range of about 200° to about 500° C. Preferably, the temperature is in the range of about 250° to about 400° C.

The process can be conducted in either vapor or liquid phase. Conducting the process in liquid phase requires sufficient pressure to keep the reactants in the liquid state (usually about 7 to 70 atmospheres).

The reaction time is related to space velocity which has been defined in the foregoing.

While the process can be conducted as a batch operation, preferably it is conducted as a continuous process.

The desired products can be recovered from the reaction admixture by fractional distillation.

While we believe it is understood by those skilled in this art it may be well to note that when t-butylated cresols are used, isobutylene is produced as a by-product. Use of other cresols, as defined hereinbefore, results in the production of the corresponding by-product.

In the description provided herein we have stated both suitable and preferred ranges. It is to be understood that the process is operable using the suitable ranges but that better results can be obtained using the preferred ranges.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This illustrates the formation of m-cresol, 2,3,6-trimethylphenol, and 2,3- and 2,5-xylenols (which could, in principle, be remethylated to produce desirable trimethylphenols). The reaction was carried out with a 2:1 mole ratio of methanol to di-t-butyl-m-cresol, over CATAPAL SB alumina (1/16 inch extrudate), at 370° C. and 400 psig (28.2 atmospheres), with a LHSV=2.8. Isobutylene was collected in a "DRY-ICE"-cooled trap.

The composition of the feed and of the product are shown below.

| Component | Feed | Product |
|---|---|---|
| m-cresol | — | 17.3 |
| 2,5-dimethylphenol | — | 21.9 |
| 2,3,-dimethylphenol | — | 8.0 |
| 2,3,6-trimethylphenol | — | 20.5 |
| 2,3,5-trimethylphenol | — | 2.7 |
| 2,3,4,6-tetramethylphenol | — | 10.1 |
| 6-t-butyl-m-cresol | 0.3 | — |
| pentamethylphenol | — | 5.9 |
| unknowns | 5.9 | 13.5 |
| 4,6-di-t-butyl-m-cresol | 93.7 | — |

EXAMPLE 2

This illustrates the formation of m-cresol and thymol. The reaction was carried out with a 1:1 mole ratio of isopropanol to di-t-butyl-m-cresol, over CATAPAL SB alumina (1/16 inch extrudate), at 350° C. and 440 psig (30.9 atmospheres), with a LHSV=2.5. Isobutylene and propylene were collected in a "DRY-ICE"-cooled trap.

The composition of the feed and of the product are shown below.

| Component | Feed | Product |
|---|---|---|
| m-cresol | — | 58.1 |
| thymol | — | 30.1 |
| 6-t-butyl-m-cresol | 0.3 | — |
| 4,6-di-t-butyl-m-cresol | 93.7 | — |
| unknowns | 5.9 | 11.9 |

Thus, having described the invention in detail, it will be understood by those skilled in the art that certain variations and modifications may be made without departing from the spirit and scope of the invention as defined herein and in the appended claims.

We claim:

1. A method for preparing a product containing predominantly m-cresol and thymol said method comprising heating, at a temperature in the range of about 200° to about 500° C., a mixture of di-t-butyl-m-cresol and isopropanol in the presence of a catalytic amount of activated alumina.

2. The method of claim 1 wherein the alcohol and cresol feedstock are present in the range of about 0.2:1 to about 15:1, expressed as moles of alcohol to cresol.

3. The method of claim 2 wherein the amount of activated alumina, expressed as volume of total liquid per hour per volume of catalyst is in the range of about 0.1 to about 35.

* * * * *